United States Patent
Koike et al.

[11] Patent Number: 6,143,767
[45] Date of Patent: Nov. 7, 2000

[54] PIPERIDINYLAMINO TRICYCLIC COMPOUNDS AS SUBSTANCE P ANTAGONISTS

[75] Inventors: Hiroki Koike; Hiroaki Wakabayashi, both of New York, N.Y.

[73] Assignee: Pfizer Inc, New York, N.Y.

[21] Appl. No.: 09/351,011

[22] Filed: Jul. 12, 1999

Related U.S. Application Data

[62] Division of application No. 08/907,374, Aug. 7, 1997, Pat. No. 5,972,930.

[30] Foreign Application Priority Data

Aug. 14, 1996 [WO] WIPO ............... PCT/IB96/00798

[51] Int. Cl.⁷ ............... C07D 401/04; A61K 31/454; A61K 31/4545
[52] U.S. Cl. ............... 514/322; 546/199
[58] Field of Search ............... 546/199; 514/322

[56] References Cited

FOREIGN PATENT DOCUMENTS

| | | |
|---|---|---|
| 9300331 | 1/1993 | WIPO . |
| 9301170 | 1/1993 | WIPO . |
| 9404496 | 3/1994 | WIPO . |
| 9508549 | 3/1995 | WIPO . |
| 9703066 | 1/1997 | WIPO . |
| 9708144 | 3/1997 | WIPO . |

*Primary Examiner*—Alan L. Rotman
*Attorney, Agent, or Firm*—Peter C. Richardson; Paul H. Ginsburg; Roy F. Waldron

[57] ABSTRACT

This invention provides a compound of the formula:

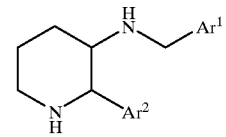

(I)

and its pharmaceutically acceptable salts, wherein
$Ar^1$ is selected from the group having the formulae:

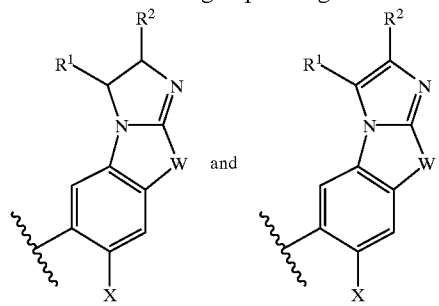

wherein,
$R^1$ and $R^2$ are independently hydrogen or $C_1$–$C_6$ alkyl;
W is $(CH_2)_a$ wherein n is from 1 to 3, or —CH=CH—;
X is $C_1$–$C_6$ alkoxy or halo $C_1$–$C_6$ alkoxy; and
$Ar^2$ is phenyl optionally substituted by halogen atom.

These compounds are useful in the treatment of a gastrointestinal disorder, a central nervous system (CNS) disorder, an inflammatory disease, emesis, urinary incontinence, pain, migraine, sunburn, angiogenesis, diseases, disorders and adverse conditions caused by *Helicobacter pylori*, or the like in a mammalian subject, especially humans.

8 Claims, No Drawings

PIPERIDINYLAMINO TRICYCLIC COMPOUNDS AS SUBSTANCE P ANTAGONISTS

This application is a divisional application of Ser. No. 08/907,374 filed Aug. 7, 1997, now U.S. Pat. No. 5,972,930, which is the U.S. national stage Section 371 of International application No. PCT/IB96/00798, filed Aug. 14, 1996.

TECHNICAL FIELD

This invention relates to novel piperidinylamino tricyclic compounds and their pharmaceutically acceptable salts, and to pharmaceutical compositions containing them. The pharmaceutically active compounds of this invention can be used as substance P antagonists.

BACKGROUND ART

Substance P is a naturally occurring undecapeptide belonging to the tachykinin family of peptides, the latter being so-named because of their prompt stimulatory action on smooth muscle tissue. More specifically, substance P is a pharmaceutically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine, as well as in central nervous system disorders such as anxiety and schizophrenia, in respiratory and inflammatory diseases such as asthma and rheumatoid arthritis, respectively, and in gastrointestinal disorders and diseases of GI tract, like ulcerative colitis and Crohn's diseases, etc. It is also reported that the tachykinin antagonists are useful for the treatment of allergic conditions, immunoregulation, vasodilation, bronchospasm, reflex or neuronal control of the viscera and senile dementia of the Alzheimer type, emesis, sunburn and Helicobacter pylori infection.

International Publications WO 93/01170, WO 95/08549 and WO 97/08144 disclose a wide variety of piperidine derivatives, as tachykinin antagonists such as substance P antagonists.

BRIEF DESCRIPTION OF THE INVENTION

The present invention provides piperidinylamino tricyclic compounds of the following chemical formula (I):

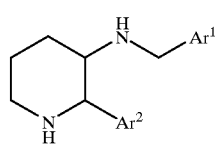

(I)

its pharmaceutically acceptable salts, wherein $Ar^1$ is selected from groups of the following formulae:

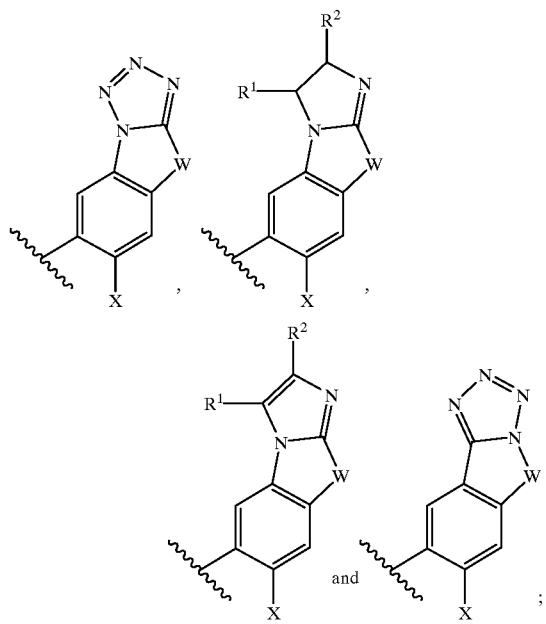

wherein, $R^1$ and $R^2$ are independently hydrogen or $C_1$–$C_6$ (preferably $C_1$–$C_3$) alkyl;

W is $(CH_2)_a$ wherein n is from 1 to 3, or —CH=CH—;

X is $C_1$–$C_6$ (preferably $C_1$–$C_3$) alkoxy or halo $C_1$–$C_6$ (preferably Cl-$C_3$) alkoxy; and $Ar^2$ is phenyl optionally substituted by halogen atom.

These compounds are useful as substance P antagonists, and thus useful as analgesics or anti-inflammatory agents, or in the treatment of allergic disorders, angiogenesis, central nervous system (CNS) disorders, emesis, gastrointestinal disorders, sunburn, urinary incontinence, and diseases, disorders and adverse conditions caused by Helicobacter pylori, or the like, in a mammalian subject, especially human. These compounds are especially useful for the treatment of CNS disorders.

Accordingly, the present invention provides a pharmaceutical composition for the prevention or treatment of a medical condition for which antagonist activity toward substance P is needed, in a mammalian subject, which comprises the compound of the formula (I) or a pharmaceutically acceptable salt thereof, and a pharmaceutically acceptable carrier. The medical condition includes allergic disorders, angiogenesis, gastrointestinal disorders, CNS disorders, inflammatory diseases, emesis, urinary incontinence, pain, migraine, sunburn, and diseases, disorders and adverse conditions caused by Helicobacter pylori in a mammalian subject.

The present invention also provides a method for the prevention or treatment of a medical condition for which antagonist activity toward substance P is needed, in a mammalian subject, which comprises administering to said subject a compound of the formula (I) or a pharmaceutically acceptable salt thereof.

DETAILED DESCRIPTION OF THE INVENTION

In this specification, the term "$C_1$–$C_6$ alkoxy" is used herein to mean a straight or branched —OR (R is $C_1$–$C_6$ alkyl) including, but not limited to, methoxy, ethoxy, propoxy, isopropoxy, n-butoxy, isobutoxy, tert-butoxy and the like.

The term "halogen atom" is used herein to mean F, Cl, Br and I.

The term "halo $C_1$–$C_6$ alkoxy" is used herein to mean a $C_1$–$C_6$ alkoxy radical substituted with one or more halogen atoms including, but not limited to, difluoromethoxy, trifluoromethoxy, 2,2,2-trifluoroethoxy and the like.

In the preferable embodiment of the present invention, X is methoxy, $Ar^2$ is phenyl and n is 2 or 3.

In these compounds, preferable stereochemistry of 2-$Ar^2$ and 3-NH—$CH_2$—$Ar^1$ is (2S, 3S).

Preferred individual compounds of this invention are the following:

(2S,3S)-3-[(7-methoxy-4,5-dihydro-[1,2,3,4]tetrazolo[1,5-a]quinolin-8-yl)methyl]amino-2-phenylpiperidine or its salts;

(2S,3S)-3-[(9-methoxy-6,7-dihydro-5H-[1,2,3,4]tetrazolo[5,1-a][2]benzazepin-10-yl)methyl]amino-2-phenylpiperidine or its salts; and (2S,3S)-3-[(7-methoxy-1,2,4,5-tetrahydroimidazo[1,2-a]quinolin-8-yl) methyl]amino-2-phenylpiperidine or its salts.

General Synthesis

The piperidine compounds of the formula (I) of this invention may be prepared as described in the following reaction schemes.

Unless otherwise indicated, in the reaction schemes that follow, $Ar^1$, $Ar^2$, X and n are defined as above.

Scheme 1 illustrates the preparation of compounds of the formula (I).

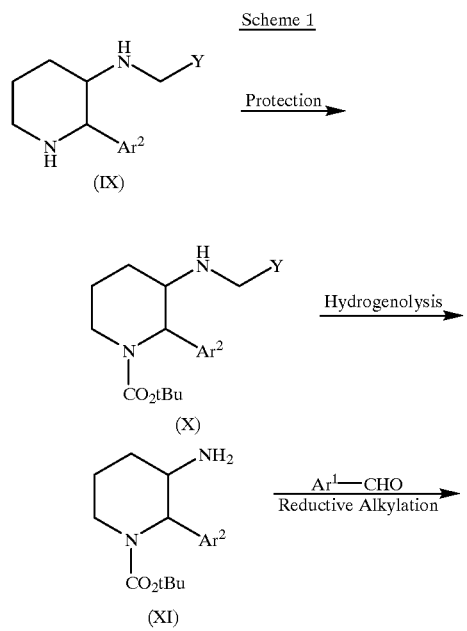

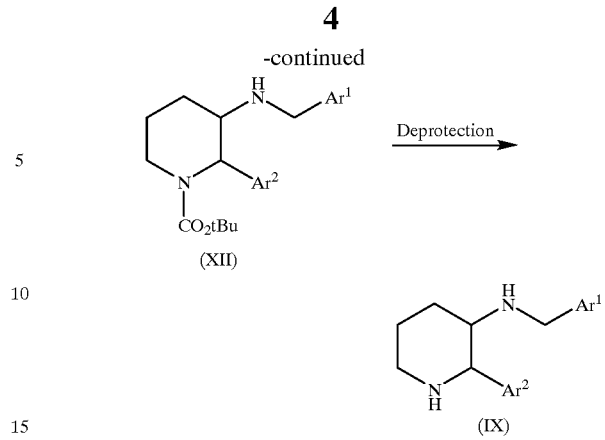

Referring to Scheme 1, N-protection of a compound of the formula (IX) ($Ar^2$ is phenyl or the like and Y is for example 2-methoxyphenyl) may be carried out by treatment with $(t-BuOCO)_2O$ ($Boc_2O$) in the presence of a base such as sodium bicarbonate ($NaHCO_3$) or triethylamine ($Et_3N$) to obtain a compound of the formula (X). An alternative route for N-protection of a compound of the formula (IX) may be carried out by treatment with carbobenzoxy chloride (Cbz—Cl) in the presence of a base such as sodium bicarbonate ($NaHCO_3$) or triethylamine ($Et_3N$). Compound (IX) is known or can be prepared by known methods, for example according to a method described in International Publication No. WO93/01170. Compound (X) is subjected to hydrogenolysis to obtain a compound of the formula (XI). The hydrogenolysis may be carried out by treatment with $H_2$ or ammonium formate ($HCO_2NH_4$) in the presence of a metal catalyst such as a palladium on charcoal (e.g., 20% palladium on charcoal) in a suitable solvent.

Then, the compound (XI) is subjected to reductive alkylation with $Ar^1$—CHO, selected from the groups of the formulae (W, X, $R^1$ and $R^2$ are defined above):

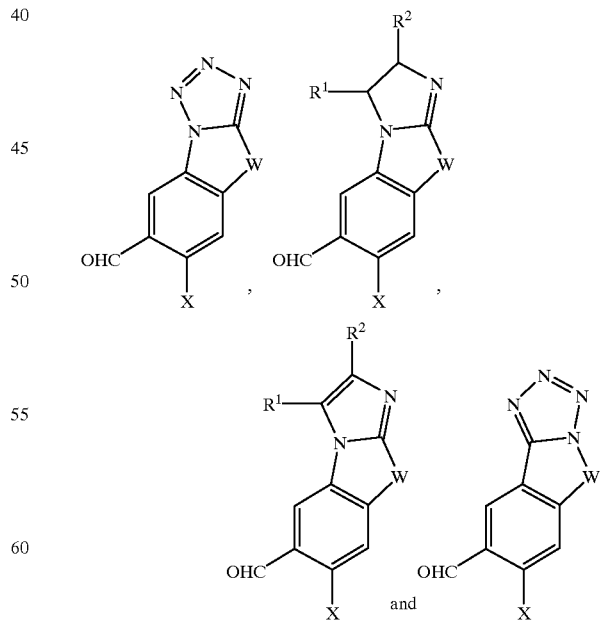

to obtain a compound of the formula (XII). This reaction can be carried out in the presence of hydride reagents include borohydrides such as sodium borohydride ($NaBH_4$), sodium cyanoborohydride (NaBH₃CN) and sodium triacetoxyborohydride (NaB(OAc)₃H), borans, aluminum-based reagents and trialkylsilanes. Suitable solvents include polar solvents such as methanol, ethanol, methylene chloride, tetrahydrofuran (THF), dioxane and ethylacetate. This reaction is typically carried out at a temperature from −78° C. to reflux temperature of the solvent, preferably 0° C. to 25° C. for 5 minutes to 48 hours. The compound (XII) may be converted into a compound of the formula (I) by treatment with acid catalyst such as hydrochloride (HCl) in methanol, concentrated (conc.) HCl in ethylacetate or CF₃CO₂H in dichloroethan under suitable conditions.

Further, compound, Ar¹—CHO as mentioned above can be prepared by direct or indirect formylation of a corresponding tetrazole compound (III-a) or (III-b) or a imidazole compound (III-c) as shown below.

Any formylation methods known to those skilled in the art may be used to introduce a formyl group into a benzene ring. For example, direct formylation may be accomplished by contacting the quinoline or benzazepin compound with a suitable formylating agent in the presence of a suitable catalyst. Suitable formylating agent/catalyst systems include dichloromethyl methyl ether/titanium (IV) chloride (Cl₂CHOCH₃/TiCl₄), trifluoroacetic acid (CF₃CO₂H)/ hexamethylenetetamine (modified Duffs conditions) and phosphoryl trichloride (POCl₃)/DMF (Vilsmeier's conditions). Indirect formylation may be achieved by halogenating the quinoline or benzoazepin compound, displacing the halogen atom introduced with a cyano group, and then subjecting the resultant cyano-substituted compound to reduction. The halogenation as used herein may be carried out according to the procedure reported in G. A. Olah et al. *J. Org Chem*, Vol. 58, p. 3194, 1993. The displacement of the halogen atom with a cyano group may be performed according to the methods reported in D. M. Tschaem et al., *Synth Commun*, Vol. 24., p. 887, 1994 or K. Takagi et al., *Bull Chem. Soc. Jpn*. Vol. 64, p. 1118, 1991. The reduction as used herein may be performed in the presence of diisopropyl aluminiumhydride (DIBAL-H) in dichloromethane or Raney nickel in formic acid.

Scheme 2 illustrates methods for preparing a compound of the formula (III-a), (III-b) or (III-c).

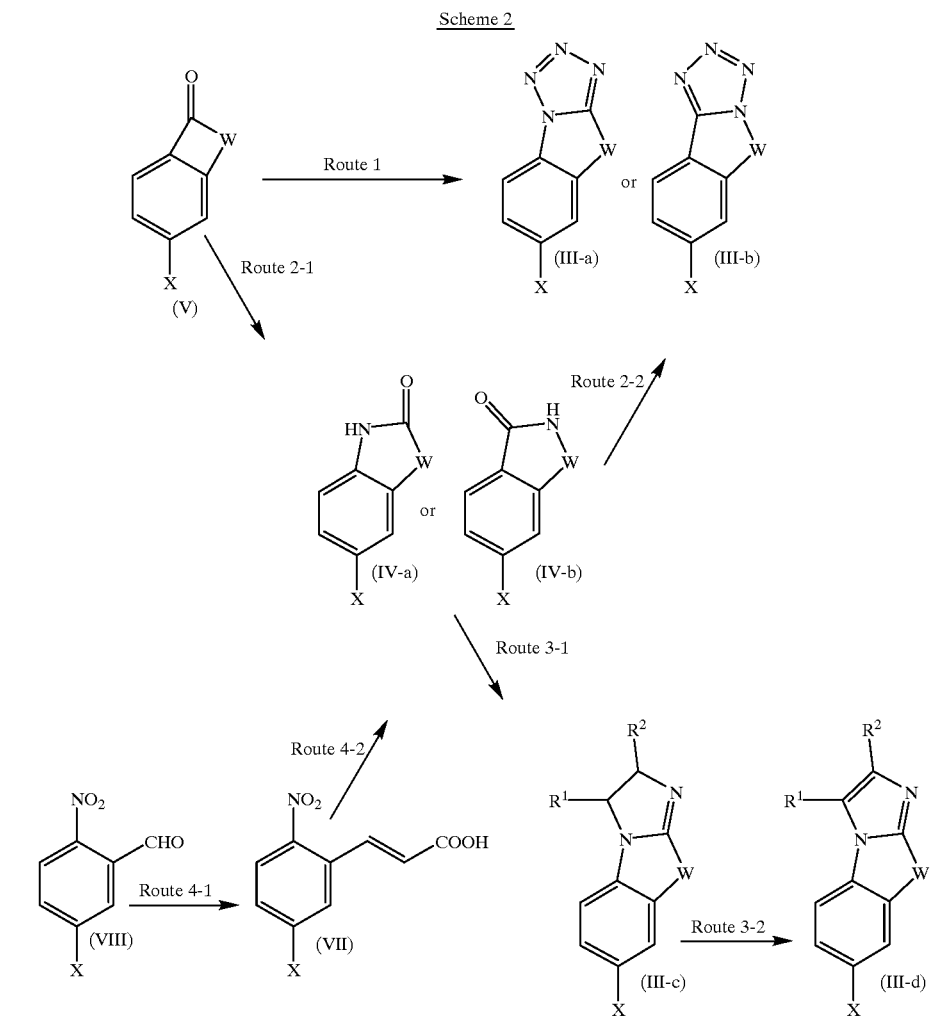

A tetrazole compound (III-a) or (III-b) can be prepared by reacting a corresponding compound of the formula (V), such as 1-indanone or 1-tetralone derivative, with sodium azide or potassium azide in the presence of an acid catalyst such as sulfonic acid (Route 1). This reaction can be carried out for example in a reaction inert solvent such as dichloromethane, at a temperature from −50° C. to reflux temperature of the solvent, preferably from 0° C. to 25° C. for 10 minutes to 48 hours, preferably 30 minutes to 3 hours.

Alternatively, the tetrazole compound (III-a) or (III-b) can be prepared from a compound (IV-a) or (IV-b) with $POX_3$ (X is Cl or Br) alone or in the presence of $PX_5$, and further reaction of the reaction mixture with sodium azide or potassium azide to give the compound (III-a) or (III-b) (Route 2-2, reported for example in Japanese Unexamined Patent Publication Gazette No. 52-57195). The compound of (IV-a) or (IV-b) can be reacted with Lawesson's Reagent in a reaction inert solvent, such as toluene, at reflux temperature for 5 minutes to 24 hours to exchange oxo group of the compound (IV-a) or (IV-b) with thioxo group. Then the thioxo compound can be reacted with hydrazine, preferably in a poler solvent, such as water, methanol or ethanol at a temperature from 0° C. to 100° C. for 5 minutes to 24 hours, followed by a reaction with nitrous acid for example in water in the presence of acid such as acetic acid at a temperature from −15° C. to 15° C. for 5 minutes to 24 hours to give the compound of (III-a) or (III-b).

The intermediate (IV-a) or (IV-b) may also be reacted with diethyl azodicarboxylate (DEAD) in the presence of triphenylphosphine ($Ph_3P$) in a reaction inert solvent such as azidotrimethylsilane ($TMSN_3$) to give the compound of (III-a) or (III-b) (J. V. Duncia et al., *J. Org. Chem.* 1991, Vol. 56, pp. 2395–2400).

The compound (IV-a) or (IV-b) can be prepared by subjecting a compound (V) to the Schmidt reaction (Route 2-1, reported in for example *March's Advanced Org. Chem.*, p. 986–987). The Schmidt reaction can be carried out at a temperature from −50° C. to reflux temperature of the solvent for 10 minutes to 48 hours.

The intermediate of the formula (IV-a), wherein n is 2, may be prepared by reacting a nitrobenzaldehyde (VIII) with malonic acid in the presence of pyridine in a reaction inert solvent such as ethanol to give a compound (VII) (Route 4-1), followed by a conventional hydrogenation, for example, using a metal catalyst such as a palladium on charcoal (Route 4-2) (G. H. Jones et. al., *Journal of Medicinal Chemistry*, Vol. 30, No.2, pp. 295–303, 1987). The reaction of the compound (VIII) with malonic acid in the presence of pyridine can be carried out by heating the mixture at the solvent reflux temperature for 30 minutes to 3 days. Then, the intermediate (IV-a) can be reacted with a corresponding ethylenediamine in the presence of toluene-p-sulfonic acid (p-TsOH) to give the compound (III-c) (Route 3-1) according to the methods reported in R. F. Cookson et al., *J. S. C. Perkin I*, p. 1850, 1975. This reaction is typically carried out without solvent or in a reaction inert solvent such as xylene at a temperature of 100° C. to 250° C. for 30 minutes to 48 hours. The compound of formula (III-c) can be oxidized to give a compound of (III-d) (Route 3-2) under suitable conditions known to a skilled person. This reaction can be carried out in the presence of a metal catalyst such as Raney nickel in a reaction inert solvent such as methanol or ethanol, or in the presence of an oxidizing agent such as $KMnO_4$ or $MnO_2$ in a reaction inert solvent such as acetone, benzene or toluene.

Starting materials of the formula (V) and (VIII) are either known, or may be prepared according to conventional procedures known for the preparation of analogous compounds.

The compounds of formula (I), and the intermediates shown in the above reaction schemes can be isolated and purified by conventional procedures, such as recrystallization or chromatographic separation.

As the piperidine compounds of this invention possess at least two asymmetric centers, they are capable of occurring in various stereoisomeric forms or configurations. Hence, the compounds can exist in separated (+)- and (−)-optically active forms, as well as mixtures thereof. The present invention includes all such forms within its scope. Individual isomers can be obtained by known methods, such as optical resolution, optically selective reaction, or chromatographic separation in the preparation of the final product or its intermediate.

In so far as the piperidine compounds of this invention are basic compounds, they are all capable of forming a wide variety of different salts with various inorganic and organic acids. Although such salts must be pharmaceutically acceptable for administration to animals, it is often desirable in practice to initially isolate the piperidine base compound from the reaction mixture as a pharmaceutically unacceptable salt and then simply convert to the free base compound by treatment with an line reagent and thereafter convert the free base to a pharmaceutically acceptable acid addition salt. The acid addition salts of the piperidine base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained. The acid which are used to prepare the pharmaceutically acceptable acid addition salts of the aforementioned piperidine base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate))salts.

The piperidine compounds of the invention which have also acidic groups are capable of forming base salts with various pharmaceutically acceptable cations. Examples of such salts include the alkali metal or alkaline-earth metal salts and particularly, the sodium and potassium salts. These salts are all prepared by conventional techniques.

The chemical bases which are used as reagents to prepare the pharmaceutically acceptable base salts of this invention are those which form non-toxic base salts with the herein described acidic piperidine derivatives. These particular non-toxic base salts include those derived form such pharmaceutically acceptable cations as sodium, potassium, calcium and magnesium, etc. These salts can easily be prepared by treating the aforementioned acidic piperidine compounds with an aqueous solution containing the desired pharmaceutically acceptable cation, and then evaporating the resulting solution to dryness, preferably under reduced pressure. Alternatively, they may also be prepared by mixing lower alkanoic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The active piperidine compounds of the present invention exhibit significant substance P receptor-binding activity and therefore, are of value in the treatment of a wide variety of clinical conditions which are characterized by the presence of an excess of said substance P activity. Such conditions include gastrointestinal disorders, central nervous system disorders, inflammatory diseases, emesis, urinary incontinence, pain, migraine or angiogenesis in a mammalian subject, especially humans. For treatment of emesis, these compounds may preferably be used in combination with a 5HT$_3$ receptor antagonist.

The active piperidine compounds of the formula (I) of this invention can be administered via either the oral, parenteral or topical routes to mammals. In general, these compounds are most desirably administered to humans in doses ranging from about 0.3 mg up to 750 mg per day, although variations will necessarily occur depending upon the weight and condition of the subject being treated and the particular route of administration chosen. However, a dosage level that is in the range of from about 0.06 mg to about 2 mg per kg of body weight per day is most desirably employed. Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging about 5.0% to about 70% by weight.

For oral administration, tablets containing various excipient such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention, as substance P antagonists, is determined by their ability to inhibit the binding of substance P at its receptor sites in CHO-cells which reveal NK1 receptor or IM-9 cells employing radioactive reagents. The substance P antagonist activity of the herein described piperidine compounds is evaluated by using the standard assay procedure described by D. G. Payan et al., as reported in *The Journal of Immunology*, Vol. 133, p. 3260, 1984. This method essentially involves determining the concentration of the individual compound required to reduce by 50% the amount of radiolabelled substance P reagents at their receptor sites in said isolated cow tissues or IM-9 cells, thereby affording characteristic IC$_{50}$ values for each compound tested. More specifically, inhibition of [$^3$H]SP binding to human IM-9 cells by compounds are determined in assay buffer (50 mM Tris-HCl (pH 7.4), 1 mM MnCl$_2$, 0.02 % bovine serum albumin, bacitracin (40 $\mu$g/ml), leupeptin (4 $\mu$g/ml), chymostatin (2 $\mu$g/ml) and phosphoramidon (30 $\mu$g/ml)). The reaction is initiated by the addition of cells to assay buffer containing 0.56 nM [$^3$H]SP and various concentrations of compounds (total volume; 0.5 ml) and allowed to incubate for 120 min at 4° C. Incubation is terminated by filtration onto GF/B filters (presoaked in 0.1% polyethylenimine for 2 hours). Nonspecific binding is defined as the radioactivity remaining in the presence of 1 $\mu$M SP. The filters are placed into tubes and counted using liquid scintillation counter. Some compounds, prepared in the working examples as described below, were tested in accordance with the above procedures, and showed good binding activities (i.e., IC$_{50}$ value of 0.1 to 50 $\mu$M).

The adverse effect on Ca$^{2+}$ channel binding affinity is determined by study of verapamil binding in a rat heart membrane preparation. More specifically, verapamil binding is performed as previously described by Reynolds et al., (*J. Phannacol. Exp. Ther.* Vol. 237, p. 731, 1986). Briefly, incubations are initiated by the addition of tissue to tubes containing 0.25 nM [$^3$H]desmethoxyverapamil and various concentrations of compounds (total volume; 1 ml). Nonspecific binding is defined as radioligand binding remaining in the presence of 3–10 $\mu$M methoxyverapamil.

The activity of the compounds of this invention against CNS disorders is determined in a [Sar$^9$, Met(O$_2$)$^{11}$] substance P-induced tapping test in gerbils. More specifically, gerbils are lightly anesthetized with ether and the skull surface is exposed. [Sar$^9$, Met(O$_2$)$^{11}$]substance P or vehicle (5 $\mu$l) are administered directly into the lateral ventricles via a 25 gauge needle inserted 3.5 mm below lambda. Following injection, gerbils are placed in 2 liter beaker individually and monitored for repetitive hind paw tapping. Some compounds prepared in the following Examples were tested in accordance with these testing methods. As a result, it was found that the compounds of the present inventions have good antagonist activity toward substance P, particularly good activity against CNS disorders with favorable metabolical properties.

The anti-inflammatory activity of the compounds of this invention is demonstrated by a capsaicin-induced plasma extravasation test. In this test, anti-inflammatory activity is determined as the percent inhibition of plasma protein extravasation in the ureters of male Hartley guinea pigs (weighing 300–350 g). Plasma extravasation is induced by intraperitoneal injection of capsaicin (30 μM in 0.1% BSA containing buffer, 10 ml/animal) into the guinea pigs pentobarbital-anesthetised 25 mg/kg i.p.) and fasted overnight. Test compounds are dissolved in 0.1% methyl cellulose-water and given orally 1 hour before capsaicin challenge. Evans blue dye (30 mg/kg) is administered intravenously 5 minutes before the challenge. The animals are killed 10 minutes after capsaicin injection and both right and left ureter are removed. Tissue dye content is quantitated after overnight formamide extraction at 600 nm absorbance. This test method is known in the literature (A. Nagahisa et al., *European Journal of Pharmacology*, Vol. 217, pp. 191–195, 1992).

The half life of the compounds of this invention is determined in a human liver microsome preparation. More specifically, the compound (1 μM) was incubated with pooled human liver microsome (2.0 mg/ml), NADP (1.3 mM), NADH (0.93 mM), glucose-6-phosphate (3.3 mM) $MgCl_2$ (3.3 mM), and glucose-6-phosphate dehydrogenase (8 units/ml) in a total volume of 1.2 ml 100 mM potassium phosphate buffer, pH 7.4. At various time points (0, 5, 10, 30 and 60 min), a 100 μl sample was added to acetonitrile solution (1.0 ml), which included an internal standard. The precipitated protein was spun down in a centrifuge (3,000× g, 5 min). The supernatant was analyzed by LC-MS. LC-MS unit was consisted of Hewlett Packard HP1090 HPLC system and Sciex API-III. Samples(10 μl) were injected by means of autosampler, onto Hewlett Packard ODS-Hypersil column (2.1×20 mm). A mobile phase was consisted of 80% acetonitrile in 10 mM ammonium acetate. The measurement of API-III was analyzed with multiple reacting monitoring (MRM) detection.

EXAMPLES

The present invention is illustrated by the following examples. However, it should be understood that the invention is not limited to the specific details of these examples. Melting points were taken with a Buchi micro melting point apparatus and uncorrected. Infrared Ray absorption spectra (IR) were measured by a Shimadzu infrared spectrometer (IR-470). $^1$H nuclear magnetic resonance spectra (NMR) was measured in $CDCl_3$ by a JEOL NMR spectrometer (JNM-GX270, 270 MHz for $^1$H) unless otherwise indicated and peak positions are expressed in parts per million (ppm) downfield from tetramethylsilane. The peak shapes are denoted as follows: s, singlet; d, doublet; t, triplet; m, multiplet.

Example 1

Preparation of (2S,3S)-3-[(7-methoxy-4,5-dihydro-[1,2,3,4]tetrazolo[1,5-a]quinolin-8-yl)methyl]amino-2-phenylpiperidine dihydrochloride (Compound 8)

(i) 7-Methoxy-4,5-dihydro-[1,2,3,4]tetrazolo[1,5-a]quinoline (Compound 1)

This compound was prepared according to the procedures described in Japanese Unexamined Patent Publication Gazette No. 52-57194.

(ii) 7-Methoxy-4,5-dihydro-[1,2,3,4]tetrazolo[1,5-a]quinoline-8-carboxaldehyde (Compound 2)

To a stirred solution of Compound 1 (160 mg, 0.79 mmol) in TFA (16 ml) was added hexamethylenetetramine (1.1 g, 7.9 mmol), and refluxed for 3 days. The solvent was evaporated, and the residue was diluted with AcOEt. This organic layer was washed with water and brine, dried over $MgSO_4$, filtered, and concentrated. This was purified by $SiO_2$ chromatography to give Compound 2 (90 mg, 0.39 mmol, 50%) as a white solid.

$^1$H-NMR (270 MHz) δ($CDCl_3$) 10.46 (1H, s), 8.45 (1H, s), 7.03 (1H, s), 4.02 (3H, s), 3.42–3.34 (2H, m), 3.26–3.17 (2H, m) ppm.

(iii) (2S,3S)-3-(2-Methoxybenzyl)amino-2-phenylpiperidine dihydrochloride (Compound 3)

This compound was prepared according to the procedures described in WO93/01170.

(iv) (2S,3S)-1-tert-Butoxycarbonyl-3-(2-methoxybenzyl)amino-2-phenylpiperidine (Compound 4)

To a stirred and ice-cooled mixture of Compound 3 (10.0 g, 27.1 mmol), 3.0 M NaOH aq. (36.1 ml, 108.4 mmol) and tert-BuOH (15.0 ml) was added (tert-BuOCO)$_2$O (Boc$_2$O, 7.39 g, 33.8 mmol). After stirring at room temperature overnight, the mixture was extracted with AcOEt (×3). The combined AcOEt extracts were washed with sat. NaHCO$_3$ and brine, dried over Na$_2$SO$_4$, and concentrated to give Compound 4 (11.3 g, quant.) as a pale yellow syrup.

IR (film) 3350, 1693, 1605, 1590, 1492, 755 cm$^{-1}$; $^1$H-NMR (270 MHz) δ($CDCl_3$) 7.58 (2H, br.d,J=7.3 Hz), 7.36–7.16 (5H, m), 6.89 (1H, ddd,J=7.5, 7.5, 1.1 Hz), 6.81 (1H, dd,J=8.4, 0.8 Hz), 5.47 (1H, br.s), 3.96 (1H, dm,J=13.4 Hz), 3.87 (1H, d,J=13.6 Hz), 3.79 (1H, d,J=13.6 Hz), 3.70 (3H, s), 3.10–2.99 (1H, m), 2.94 (1H, dd,J=12.5, 3.4 Hz), 1.87–1.74 (2H, m), 1.74–1.40 (3H, m), 1.41 (9H, s) ppm.

This was employed in the next step without further purification.

(v) (2S,3S)-3-Amino-1-tert-butoxycarbonyl-2-phenylpiperidine (Compound 5)

A mixture of Compound 4 (11.3 g), 20% Pd(OH)$_2$/C (Pearlman's catalyst, 3.7 g), and MeOH (90 ml) was stirred under an atmosphere of H$_2$ (balloon) at room temperature for 4 days. The catalyst was filtered off by the aid of celite, and washed with MeOH. The combined solvents were concentrated to give crude Compound 5 (8.59 g, quant.).

This was dissolved in i-propanol (20 ml), and then a warmed solution of fumaric acid (1.57 g, 13.5 mmol) in i-propanol (20 ml) was added in one portion to this solution at room temperature. When the mixture was scratched with a spatula, there took place precipitation of white solids with ease. After the mixture was left to stand at 4° C. in a refrigerator overnight, the crystals precipitated were collected by filtration, washed with ice-chilled i-propanol, and dried in vacuo at 50° C. to give a first crop of (2S,3S)-3-amino-1-(tert-butoxycarbonyl)-2-phenylpiperidine semifumarate Compound 6 (6.14 g, 68%) as white short needles. The combined filtrate and washing were concentrated to give a residual solid (4.56 g), which was recrystallized from i-propanol and i-Pr$_2$O to give a second crop of Compound 6 (1.25 g, 13.7%).

mp 165.7–168.8° C.; Anal.% Calc for $C_{18}H_{26}N_2O_4 \cdot 0.4H_2O$: C; 63.29, H; 7.91, N; 8.20. Found: C; 63.64, H; 8.22, N; 7.79.

After a suspension of Compound 6 (1.24 g, 3.71 mmol) in H$_2$O was ice-cooled, 20% NaOH aq. was added until the mixture became basic. The mixture was then extracted with AcOEt (x3). The combined AcOEt extracts were washed with sat. NaCl aq., dried over Na$_2$SO$_4$, and concentrated to give pure Compound 5 (0.95 g, 93.1%). IR (film) 3370, 3310, 1695, 1682, 1807, 1590, 1494, 1250, 1180, 1150, 756, 703 cm$^{-1}$ $^1$H-NMR (270 MHz) δ(CDCl$_3$) 7.47–7.39 (2H, m), 7.37–7.23 (5H, m), 5.19 (1H, br.d,J=6.2 Hz), 4.00 (1H, dm, J=13.0 Hz), 3.25–3.05 (2H, m), 1.94–1.83 (1H, m), 1.83–1.56 (4H, m), 1.36 (9H, s), 1.32 (2H, br.s) ppm.

(vi) (2S,3S)-1-tert-Butoxycarbonyl-3-[(7-methoxy-4, 5-dihydro[1,2,3,4]tetrazolo[1,5-a]quinolin-8-yl) methyl]amino-2-phenylpiperidine (Compound 7)

To a stirred solution of Compound 2 (65 mg, 0.28 mmol) and Compound 5 (78 mg, 0.28 mmol) in CH$_2$Cl$_2$ (5 ml) was added NaB(OAc)$_3$H (119 mg, 0.56 mmol), and stirred for 3 h. The mixture was quenched by the addition of sat. NaHCO$_3$, and extracted with CH$_2$Cl$_2$. The organic layers were combined, dried over MgSO$_4$, filtered, and concentrated. This was purified by SiO$_2$ chromatography to give 7 (110 mg, 0.23 mmol, 82%) as a colorless oil.

$^1$H-NMR (270 MHz) δ(CDCl$_3$) 7.90 (1H, s), 7.62–7.54 (2H, m), 7.37–7.22 (3H, m), 6.77 (1H, s), 5.51–5.43 (1H, m), 4.01–3.85 (3H, m), 3.77 (3H, s), 3.35–3.28 (2H, m), 3.16–2.95 (4H, m), 1.97–1.40 (4H, m), 1.40 (9H, s) ppm.

(vii) (2S,3S)-3-[(7-Methoxy-4,5-dihydro-[1,2,3,4] tetrazolo[1,5-a]quinolin-8-yl)methyl]amino-2-phenylpiperidine dihydrochloride (Compound 8)

To a stirred solution of Compound 7 (110 mg, 0.23 mmol) in AcOEt (6 ml) was added an excess amount of HCl—MeOH, and stirred for 1 day. After the solvent was evaporated, the residual solid was recrystallized from MeOH—Et$_2$O. The crystals precipitated were collected by filtration, washed with Et$_2$O, and dried in vacuo at 30° C. to give Compound 8 (65 mg, 0.14 mmol, 61%) as a white solid.

mp 226–228° C. IR (KBr) 3425, 2935, 2665, 2590, 1628, 1559, 1503, 1449, 1331, 1244, 1150, 1042 cm$^{-1}$. $^1$H-NMR (270 MHz) δ(free base; CDCl$_3$) 7.66 (1H, s), 7.40–7.25 (5H, m), 6.65 (1H, s), 4.10–4.06 (1H, m), 3.71 (1H, d, J=13.9 Hz), 3.55–3.42 (2H, m), 3.52 (3H, s), 3.35–3.28 (2H, m), 3.15–2.85 (4H, m), 2.30–1.50 (4H, m) ppm. Anal. Calc for C$_{22}$H$_{26}$N$_6$O.2HCl.H$_2$O: C, 54.89%, H, 6.28%, N, 17.46%. Found: C, 54.78%, H, 5.90%, N, 17.26%.

Example 2

Preparation of (2S,3S)-3-[(9-methoxy-6,7-dihydro-5H-[1,2,3,4]tetrazolo[5,1-a][2]benzazepin-10-yl) methyl]amino-2-phenylpiperidine dihydrochloride (Compound 12)

(i) 9-Methoxy-6,7-dihydro-5H-[1,2,3,4]tetrazolo[5, 1-a][2]benzazepine (Compound 9)

To a stirred solution of 6-methoxy-1-tetralone (1.0 g, 5.7 mmol) in CH$_2$Cl$_2$ (10 ml) was added conc. H$_2$SO$_4$ (5 ml) at 0° C., and then NaN$_3$(1.0 g) was added gradually over 30 min. The mixture was warmed up to room temperature, and stirred for 3 h. The mixture was cooled, basified with NaOH aq., and extracted with CH$_2$Cl$_2$. The organic layers were combined, dried over MgSO$_4$, filtered, and concentrated. This residue was purified by SiO$_2$ chromatography to give Compound 9 (70 mg, 0.32 mmol, 5.6%) as a colorless oil.

$^1$H-NMR (270 MHz) δ(CDCl$_3$) 8.25 (1H, d, J=8.8 Hz), 6.94 (1H, dd, J=8.8, 2.6 Hz), 6.81 (1H, d, J=2.6 Hz), 4.61 (2H, t, J=6.6 Hz), 3.88 (3H, s), 3.02–2.93 (2H, m), 2.45–2.33 (2H, m) ppm.

(ii) 9-Methoxy-6,7-dihydro-5H-[1,2,3,4]tetrazolo[5, 1-a][2]benzazepine-10-carboxaldehyde (Compound 10)

This compound was prepared from Compound 9 in the same manner of Compound 2.

$^1$H-NMR (270 MHz) δ(CDCl$_3$) 10.42 (1H, s), 8.75 (1H, s), 6.92 (1H, s), 4.67–4.60 (2H, m), 4.02 (3H, s), 3.10–3.03 (2H, m), 2.50–2.38 (2H, m) ppm.

(iii) (2S,3S)-1-tert-Butoxycarbonyl-3-[(9-methoxy-6,7-dihydro-5H-[1,2,3,4]tetrazolo[5,1-a][2] benzazepin-10-yl)methyl]amino-2-phenylpiperidine (Compound 11)

This compound was prepared from Compound 10 and Compound 5 in the same manner of Compound 7.

$^1$H-NMR (270 MHz) δ(CDCl$_3$) 8.16 (1H, s), 7.60–7.54 (2H, m), 7.35–7.20 (3H, m), 6.68 (1H, s), 5.48–5.40 (1H, m), 4.59 (2H, t, J=6.6 Hz), 3.98–3.75 (3H, m), 3.76 (3H, s), 3.12–2.92 (4H, m), 2.43–2.32 (2H, m), 1.93–1.50 (4H, m), 1.40 (9H, s) ppm.

(iv) (2S,3S)-3-[(9-Methoxy-6,7-dihydro-5H-[1,2,3, 4]tetrazolo[5,1-a][2]benzazepin-10-yl)methyl] amino-2-phenylpiperidine dihydrochloride (Compound 12)

This compound was prepared from Compound 11 in the same manner of Compound 8.

mp 225–227° C. (KBr) 3425, 2945, 2670, 2500, 1619, 1500, 1453, 1417, 1160 cm$^{-1}$. $^1$H-NMR (270 MHz) δ(free base; CDCl$_3$) 8.01 (1H, s), 7.40–7.20 (5H, m), 6.55 (1H, s), 4.70–4.50 (2H, m), 4.05–3.95 (1H, m), 3.71 (1H, d, J=13.9 Hz), 3.60–3.33 (2H, m), 3.51 (3H, s), 3.05–2.80 (4H, m), 2.47–2.30 (2H, m), 2.20–1.90 (2H, m), 1.75–1.42 (2H, m) ppm. Anal. Calc for C$_{23}$H$_{28}$N$_6$O.2HCl.2H$_2$O: C, 53.80%, H, 6.67%, N, 16.37%. Found: C, 53.47%, H, 6.29%, N, 16.20%.

Example 3

Preparation of (2S,3S)-3-[(7-methoxy-1,2,4,5-tetrahydroimidazo[1,2-a]quinolin-8-yl)methyl] amino-2-phenylpiperidine trihydrochloride (Compound 17)

(i) 6-Methoxy-2-oxo-1,2,3,4-tetrahydroquinoline (Compound 13)

This compound was prepared according to the procedures described in *J. Med. Chem*, 30, 295(1987).

(ii) 7-Methoxy-1,2,4,5-tetrahydroimidazo[1,2-a] quinoline (Compound 14)

To a mixture of Compound 13 (0.50 g, 2.6 mmol) and ethylenediamine (0.88 ml, 13.1 mmol) was added p-TsOH H$_2$O (2.5 g, 13-1 mmol), and heated to 200° C. for 24 h. The cooled mixture was solved with 6N HCl, basified with NaOH aq., and extracted with CH$_2$Cl$_2$. The organic layers were combined, dried over MgSO$_4$, filtered, and concentrated. This residue was purified by SiO$_2$ chromatography to give Compound 14 (63 mg, 0.31 mmol, 12%) as a colorless oil.

$^1$H-NMR (270 MHz) δ (CDCl$_3$) 6.80–6.58 (3H, m), 4.12–3.82 (4H, m), 3.77 (3H, s), 2.98–2.82 (4H, m) ppm.

(iii) 7-Methoxy-1,2,4,5-tetrahydroimidazo[1,2-a] quinoline-8-carboxaldehyde (Compound 15)

To a stirred solution of Compound 14 (63 mg, 0.31 mmol) in CH$_2$Cl$_2$ (5 ml) was added TiCl$_4$ (0.17 ml, 1.6 mmol) at 0°

C. After the reaction mixture was stirred for 10 minutes, $Cl_2CHOMe$ (0.14 ml, 1.6 mmol) was added at 0° C., and stirred for 3 h. The mixture was quenched by the addition of water, basified with NaOH aq., and extracted with $CH_2Cl_2$. The combined $CH_2Cl_2$ extracts were dried over $MgSO_4$, filtered, and concentrated. The residue was purified by $SiO_2$ chromatography to give Compound 15 (25 mg, 35%) as a slight yellow solid.

$^1$H-NMR (270 MHz) δ(CDCl$_3$) 10.42 (1H, s), 7.02 (1H, s), 6.85 (1H, s), 4.05– 3.90 (2H, m), 3.91 (3H, s), 3.82–3.70 (2H, m), 3.00–2.92 (2H, m), 2.78–2.70 (2H, m) ppm.

(iv) (2S,3S)-1-tert-Butoxycarbonyl-3-[(7-methoxy-1,2,4,5-tetrahydroimidazo[1,2-a]quinolin-8-yl) methyl]amino-2-phenylpiperidine (Compound 16)

This compound was prepared from Compound 15 and Compound 5 in the same manner of Compound 7.

$^1$H-NMR (270 MHz) δ(CDCl$_3$) 7.63–7.55 (2H, m), 7.36–7.20 (3H, m), 6.66 (1H, s), 6.61 (1H, s), 5.55–5.42 (1H, m), 4.07–3.88 (7H, m), 3.70 (3H, s), 3.08–2.78 (6H, m), 1.92–1.50 (4H, m), 1.40 (9H, s) ppm.

(v) (2S,3S)-3-[(7-Methoxy-1,2,4,5-tetrahydroimidazo[1,2-a]quinolin-8-yl)methyl] amino-2-phenylpiperidine trihydrochloride (Compound 17)

This compound was prepared from Compound 16 in the same manner of Compound 8.

mp 226–227° C. IR(KBr) 3430, 2925, 2740, 1616, 1541, 1508, 1467, 1410, 1253 cm$^{-1}$. $^1$H-NMR (270 MHz) δ(free base; CDCl$_3$) 7.37–7.20 (5H, m), 6.53 (1H, s), 6.28 (1H, s), 3.97–3.88 (3H, m), 3.65–3.53 (3H, m), 3.47 (3H, s), 3.40 (1H, d, J=13.9 Hz), 3.33–3.22 (1H, m), 2.90–2.73 (4H, m), 2.68–2.60 (2H, m), 2.20–2.08 (1H, m), 2.03–1.80 (1H, m), 1.80–1.55 (1H, m) 1.50–1.38 (1H, m) ppm. Anal. Calc for $C_{24}H_{30}N_4O.3HCl.2.5H_2O$: C, 52.90%, H, 7.03%, N, 10.28%. Found: C, 52.50%, H, 6.64%N, 10.03%.

The chemical structure of the compounds prepared in Examples 1 to 3 are summarized in the following table.

TABLE

| Example | Ar$^1$ | Ar$^2$ |
|---|---|---|
| 1 | 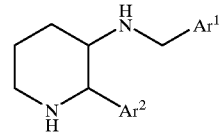 | $C_6H_6$ |
| 2 | (tetrazolo-fused benzazepine with OCH$_3$) | $C_6H_6$ |
| 3 | 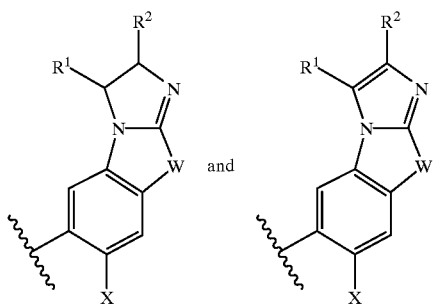 | $C_6H_6$ |

The stereochemistry of 2-Ar$^2$ and 3-NH—CH$_2$-Ar$^1$ is (2s, 3S).

What is claimed is:

1. A compound of the formula (I):

or a pharmaceutically acceptable acid addition salt thereof, wherein

Ar$^1$ is selected from the group having the formulae:

wherein,

R$^1$ and R$^2$ are independently hydrogen or $C_1$–$C_6$ alkyl;

W is (CH$_2$), wherein n is from 1 to 3, or —CH═CH—;

X is $C_1$–$C_6$ alkoxy or halo $C_1$–$C_6$ alkoxy; and

Ar$^2$ is phenyl optionally substituted by a halogen atom.

2. A compound according to claim 1, wherein X is methoxy; and Ar$^2$ is phenyl.

3. A compound according to claim 2, wherein n is 2 or 3.

4. A compound according to claim 3 which is
(2S,3S)-3-[7-methoxy-1,2,3,4-tetrahydroimidazo[1,2a]quinolin-8-yl)methyl]amino-2-phenylpiperidine or a pharmaceutically acceptable acid addition salt thereof.

5. A pharmaceutical composition for the treatment of a medical condition for which antagonist activity toward substance P is needed, in a mammalian subject, which comprises a therapeutically effective amount of a compound according to claim 1 or a pharmaceutically acceptable salt thereof, and a pharmaceutically acceptable carrier.

6. A pharmaceutical composition according to claim 5, wherein the medical condition is selected from allergic disorders, angiogenesis, gastrointestinal disorders, central nervous system disorders, inflammatory diseases, emesis, urinary incontinence, pain, migraine, sunburn, and diseases, disorders and adverse conditions caused by *Helicobacter pylori* in a mammalian subject.

7. A method for the prevention or the treatment of a medical condition for which antagonist activity toward substance P is needed, in a mammalian subject, which comprises administering to said subject a therapeutically effective amount of a compound according to claim 1 or a pharmaceutically acceptable salt thereof.

8. A method according to claim 7, wherein the medical condition is selected from allergic disorders, angiogenesis, gastrointestinal disorders, central nervous system disorders, inflammatory diseases, emesis, urinary incontinence, pain, migraine, sunburn, and diseases, disorders and adverse conditions caused by *Helicobacter pylori* in a mammalian subject.

* * * * *